(12) United States Patent
Castillo et al.

(10) Patent No.: US 7,578,800 B2
(45) Date of Patent: *Aug. 25, 2009

(54) TETHER MEMBER CONNECTING A KNEE BRACE TO A BOOT

(75) Inventors: David Castillo, Mission Viejo, CA (US); James Castillo, Los Almos, CA (US)

(73) Assignee: Asterisk.Asterisk, LLC, Lake Forest, CA (US)

( * ) Notice: Subject to any disclaimer, the term of this patent is extended or adjusted under 35 U.S.C. 154(b) by 177 days.

This patent is subject to a terminal disclaimer.

(21) Appl. No.: 11/599,535

(22) Filed: Nov. 14, 2006

(65) Prior Publication Data

US 2007/0232975 A1 Oct. 4, 2007

Related U.S. Application Data

(63) Continuation-in-part of application No. 11/396,886, filed on Apr. 3, 2006, now Pat. No. 7,458,949.

(51) Int. Cl.
*A61F 5/00* (2006.01)
*A61F 5/37* (2006.01)
*A61F 5/14* (2006.01)
*A41D 13/00* (2006.01)

(52) U.S. Cl. .................... 602/23; 602/5; 602/26; 602/27; 128/882; 36/140; 2/22

(58) Field of Classification Search ............... 24/3.13, 24/298, 300, 301, 302; 602/23, 27, 28, 29, 602/5, 6, 16, 24, 26, 62; 36/89, 140; 2/22, 2/23, 24, 911; 128/882, 869, 892
See application file for complete search history.

(56) References Cited

U.S. PATENT DOCUMENTS

| | | | |
|---|---|---|---|
| 2,883,982 | A | 4/1959 | Rainey |
| 3,900,898 | A | 8/1975 | Ackerman |
| 3,902,482 | A | 9/1975 | Taylor |
| 3,928,872 | A | 12/1975 | Johnson |

(Continued)

*Primary Examiner*—Patricia Bianco
*Assistant Examiner*—Ophelia Hawthorne
(74) *Attorney, Agent, or Firm*—Stetina Brunda Garred & Brucker

(57) ABSTRACT

The invention provides a device for protecting ligaments in a knee joint of a user. The device includes a knee brace positionable about a knee joint of a user and a boot wearable on a foot of a user. Additionally, the device includes a flexible tether member including a first coupling element coupled to the knee brace and a second coupling element coupled to the boot. The boot and knee brace are attachable and detachable via the first and second coupling elements. The flexible tether member is adjustable in length to dispose the flexible tether member in tension at least in a portion of a maximum foot range of rotation, where the maximum foot range of rotation of the user's foot relative to the knee joint causes hyperextension of a knee ligament.

16 Claims, 3 Drawing Sheets

U.S. PATENT DOCUMENTS

| | | |
|---|---|---|
| 4,136,404 A | 1/1979 | Lange |
| 6,461,318 B2 | 10/2002 | Freeman |
| 6,464,657 B1 | 10/2002 | Castillo |
| 6,471,664 B1 * | 10/2002 | Campbell et al. ............. 602/16 |
| 6,689,080 B2 | 2/2004 | Castillo |
| 6,793,641 B2 | 9/2004 | Freeman |
| 6,796,951 B2 | 9/2004 | Freeman |
| 6,962,571 B2 | 11/2005 | Castillo |
| 7,204,819 B2 * | 4/2007 | Berger ........................ 602/26 |
| 2006/0142673 A1 * | 6/2006 | Shelbourne et al. ............ 601/5 |

* cited by examiner

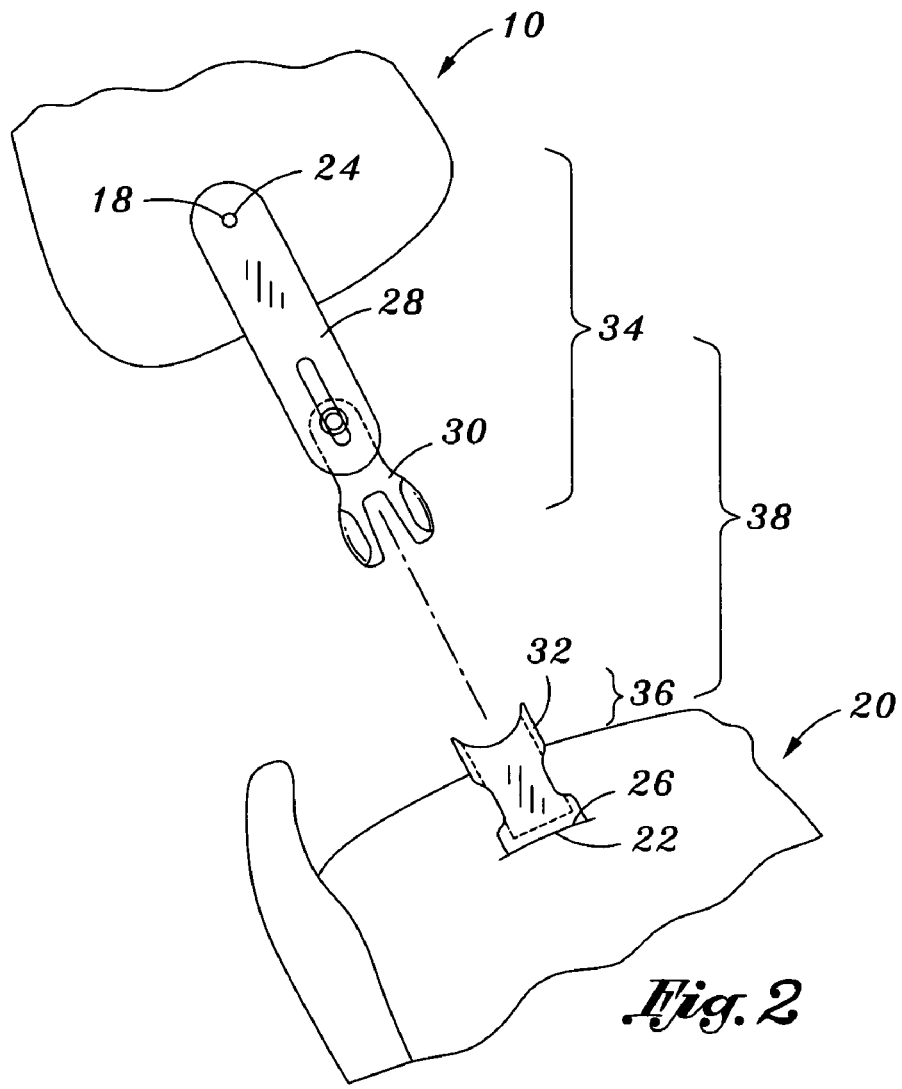
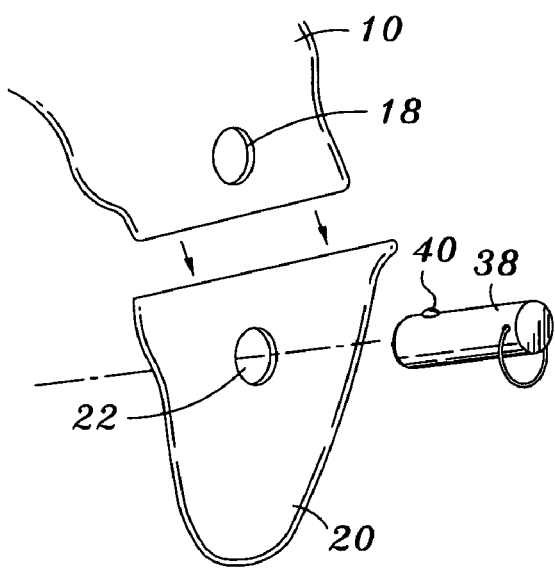 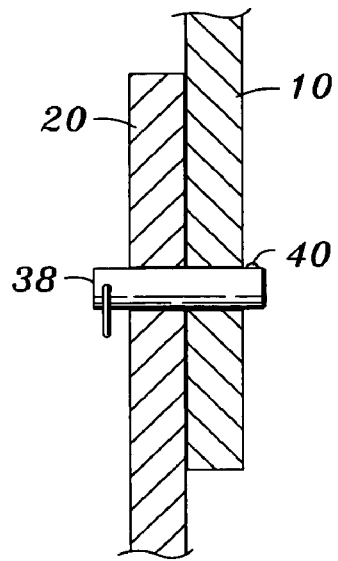

TETHER MEMBER CONNECTING A KNEE BRACE TO A BOOT

CROSS-REFERENCE TO RELATED APPLICATIONS

This application is a continuation-in-part of U.S. patent application Ser. No. 11/396,886 filed Apr. 3, 2006 now U.S. Pat. No. 7,458,949.

STATEMENT RE: FEDERALLY SPONSORED RESEARCH/DEVELOPMENT

Not Applicable

BACKGROUND

1. Field of Invention

This invention relates in general to a device for protecting the ligaments in a knee joint. Specifically, a knee brace and boot are attachable and detachable via a tether member. The tether member restricts the rotation of the knee brace relative to the boot in order to protect a user from hyperextending his knee ligaments.

2. Description

The knee joint is one of the body's most delicate joints thereby making it very prone to injury. The femur, tibia, and fibula are the bones within the leg that comprise the knee joint. These bones are stabilized by four ligaments. Two collateral ligaments located on the outside of the knee and control the lateral motion of the knee. The anterior cruciate ligament (ACL) and posterior cruciate ligament (PCL) control rotation of the knee as well as the forward and backward motion of the knee.

Injury to the knee joint can occur when at least one of the above-mentioned ligaments tears, either partially or completely. Such an injury may occur during contact or pivoting activities. For that reason, sports related activities are one of the leading causes of injury to the knee. In order to reduce one's risk of sustaining such an injury, athletes wear knee braces. Knee braces provide support to the knee joint and mitigate the stress applied to the ligaments resulting from direct contact.

One group of athletes that is particularly susceptible to knee injuries are motocross riders. Motocross is a very physically demanding sport that places a lot of stress on a rider's knees. Motocross riders maneuver their bikes at high speeds over and around obstacles and through winding courses. During a race, the rider is subjected to bumps from the other riders as well as hard landings, which may toss the rider off his bike. Rough landings and accidents may place a lot of stress on a motocross rider's knee ligaments. Therefore, most riders wear knee braces to protect their knees from injury.

Although motocross riders may injure their ligaments due to forces directly applied to the knee joint, as described above, the riders are also prone to ligament tears due to pivoting activity, which a knee brace alone may not prevent. For instance, when a rider's foot rotates or pivots independently from the rider's knee joint, a strain is applied to the knee ligaments. If the rotation of the foot is severe, the knee ligaments will hyperextend or tear. Such activity is likely to occur in motocross when a rider makes a turn. As the rider maneuvers his bike through a turn, the rider leans into the turn. Consequently, the rider's inside foot is lowered toward the dirt. On some occasions, the rider's toe catches the dirt causing the rider's foot to rotate independently from the knee joint, imparting a strain on the rider's knee ligaments, specifically the ACL.

A knee brace will not prevent a strain from being applied to the ligaments when the foot rotates independently from the knee joint. A knee brace can prevent lateral motion, as well as forward and backward motion of the knee joint, however, it is not designed to protect the ligaments from rotation. In view of these drawbacks, it is apparent that there is a need in the art for a device for protecting the ligaments in a knee joint from rotation-type injuries.

BRIEF SUMMARY

According to an aspect of the present invention, there is provided a device for protecting a user's knee ligaments. The device includes a knee brace comprising an upper frame member, a lower frame member having a brace connection point, and a joint member pivotally connected to the upper and lower frame members. The device further includes a boot wearable on the user's foot. The boot includes a boot connection point. The device further includes a tether member. The tether member comprises a first coupling element coupled to the knee brace at the brace connection point and a second coupling element coupled to the boot at the boot connection point. The boot and the knee brace are attachable and detachable via the first and second coupling elements.

It is contemplated that the tether member connects the knee brace and boot to limit one from rotating independent from the other so as to prevent injury. As such, the upper leg and lower leg of the user rotate together, thereby lessening the strain applied to the knee ligaments.

In other embodiments, the first coupling element may include a first fastening portion and a first linking portion. The first fastening portion couples the first coupling element with the knee brace at the brace connection point. In addition, the second coupling element may include a second fastening portion and a second linking portion. The second fastening portion couples the second coupling element with the boot at the boot connection point. The first and second linking portions may be cooperatively engageable. In the preferred embodiment of the present invention the first and second linking portions are male and female linking structures, where the first linking portion is a male linking structure and the second linking portion is a female linking structure.

According to another aspect of the present invention, there is provided a device for protecting ligaments in a knee joint of a motorcycle rider. The device includes a knee brace positionable about a rider's knee joint. The knee brace comprises an upper frame member, a lower frame member having a brace connection point, and a joint member pivotally connected to the upper and lower frame members. The device further includes a motorcycle boot wearable on the rider's foot, the motorcycle boot having a boot connection point. Additionally, the device also includes a tether member. The tether member couples the knee brace and the motorcycle boot at the brace and boot connection points. According to an aspect of the invention, the tether member may be a push-pin. However, the tether member may include other fastening means known by those skilled in the art, including, but not limited to a rigid strap, or a snap-fit button. Other embodiments of the present invention may include a flexible tether member. A discussion of such embodiments may be found in U.S. patent application Ser. No. 11/396,886, the disclosure of which is incorporated by reference.

The knee brace and boots described above may be used in many different applications. In many of these applications, the user may wear clothing over the knee brace. Therefore, a further aspect of the present invention is a pair of protective pants to be worn over a knee brace. The protective pants include a left pant leg, and a right pant leg coupled to the left pant leg. The protective pants further include a connection aperture or slot located on at least one of the left and right pant legs. The connection aperture allows the tether member connecting the knee brace and the boot to pass through the user's pants. According to an aspect of the present invention, the connection aperture may be located along the pant leg adjacent to the user's knee. The connection aperture may include a closing mechanism. Preferably, the closing mechanism is a zipper, but may also be a flap or button, or other appropriate closing means known in the art.

According to another aspect of the present invention, there is provided a reinforcement strip for repairing an aperture. The reinforcement is comprised of a fabric material having a bonding agent disposed thereon. The bonding agent may be glue or other fastening means known by those skilled in the art. The reinforcement strip is applied to a tear, or worn area of the aperture in order to repair the aperture.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 2 is a side view of a knee brace, boot, and a rigid tether member;

FIG. 3 is an exploded perspective view of another aspect of the present invention, showing a portion of the knee brace, boot and tether member, the tether member being a push-pin with a spring-loaded locking mechanism;

FIG. 4 is a cross-sectional view of a boot, knee brace and tether member, the tether member being a push-pin with a spring-loaded locking mechanism;

DETAILED DESCRIPTION

The ligaments holding a knee joint together are capable of withstanding a minimal level of tension. Knee ligaments are placed in tension when a person's foot rotates independently from the corresponding knee joint. If the foot rotates independently from the knee joint to a point where the knee ligaments begin to hyperextend, the rotation of the foot has exceeded a maximum foot range of rotation. The present invention is a device which limits independent rotation of the foot relative to the knee joint to prevent rotation beyond the maximum foot range of rotation.

Figure 1:
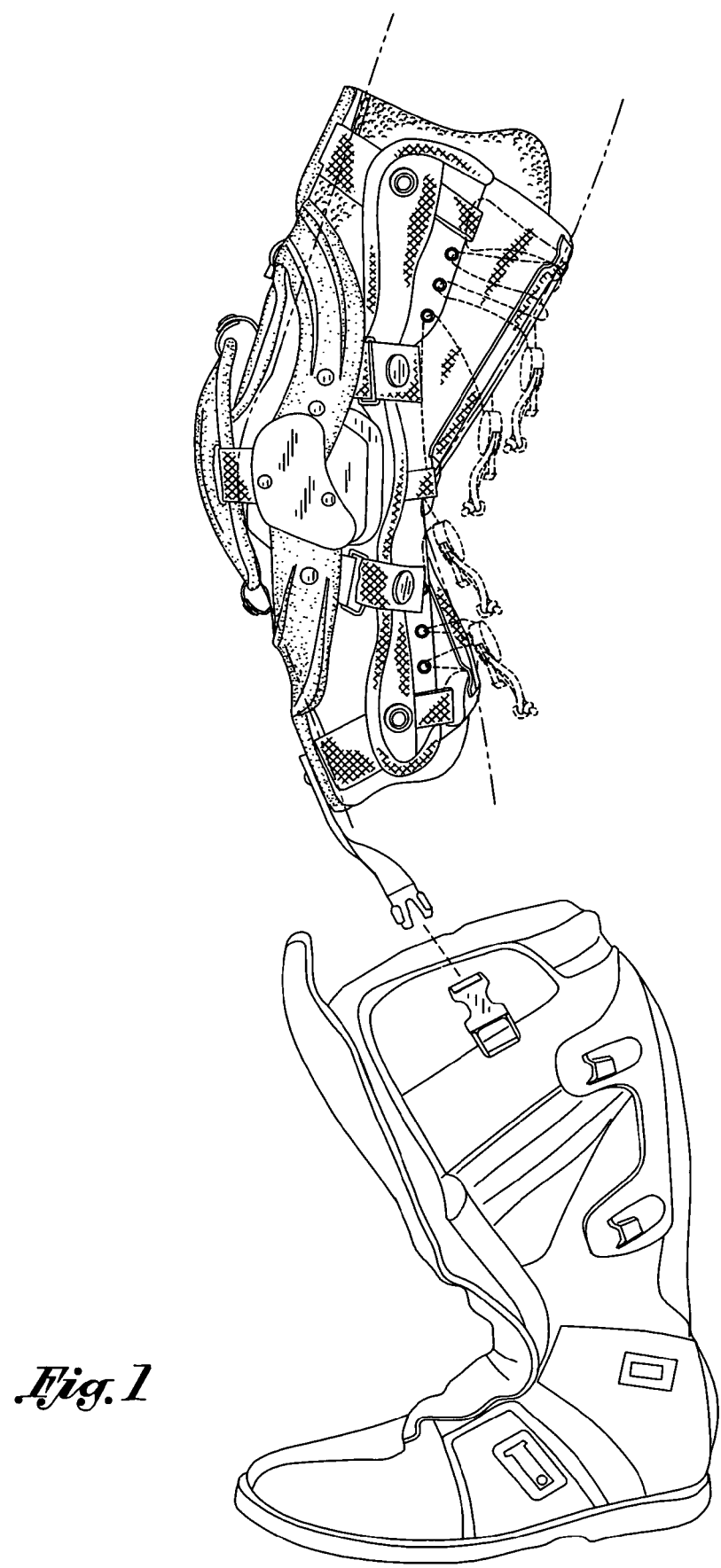
FIG. 1 is a side view of a knee brace, a boot, and a tether member according to one aspect of the invention.

Referring to FIG. 1, there is provided a device for protecting ligaments in a knee joint of a user. The device includes a knee brace 10 positionable about a user's knee joint. The knee brace 10 comprises an upper frame member 12, a lower frame member 14 having a brace connection point 18, and a joint member 16 pivotally connected to the upper and lower frame members 12, 14. The device further includes a boot 20 wearable on the user's foot, the boot 20 having a boot connection point 22. According to an embodiment of the invention, the boot 20 may be a motorcycle boot, as is shown in FIG. 1; however, other types of boots may be included within the scope of the invention. In addition, the device includes a tether member 38. The tether member 38 includes a first coupling element 34 and a second coupling element 36. The first coupling element 34 is coupled to the knee brace 10 at the brace connection point 18 and the second coupling element 36 is coupled to the boot 20 at the boot connection point 22. The boot 20 and knee brace 10 are attachable and detachable via the first and second coupling elements 34, 36.

The first coupling element 34 of the tether member 38 may further include a first fastening portion 24 and a first linking portion 30. The first fastening portion 24 couples the first coupling element 34 to the knee brace 10 at the brace connection point 18. Correspondingly, the second coupling element 36 of the tether member 38 may include a second fastening portion 26 and a second linking portion 32. The second fastening portion 26 couples the second coupling element 36 to the boot 20 at the boot connection point 22. According to various embodiments of the present invention, the first and second coupling elements 34, 36 may be fixedly coupled to the knee brace 10 and boot 20 respectively. The first coupling element 34 may be fixedly attached to the knee brace 10 via the first fastening portion 24. Likewise, the second coupling element 36 may be fixedly attached to the boot 20 via the second fastening portion 26. In such an embodiment, the first and second fastening portions 24, 26 may be a rivet, nail, or bonding agent capable of fixedly coupling the first and second coupling elements 34, 36 to the knee brace 10 and boot 20. However, there may be alternative embodiments of the invention where the first and/or second coupling elements 34, 36 are detachably coupled to the knee brace 10 or boot through the first and second fastening portions 24, 26. For example, the first and/or second fastening portions 24, 26 may be represented by a pin having a spring-loaded locking mechanism which may be placed through a hole in the knee brace 10 or boot 20, the hole being located at the brace or boot connection point 18, 22.

The location of the brace 18 and boot connection points 18, 22 may vary so long as the first coupling element 34 can connect with the second coupling element 36. Although FIG. 1 shows the brace connection point 18 on a front side of the lower frame member 14, the brace connection point 18 may be located anywhere on the lower frame member 14. In addition, FIG. 1 shows the boot connection point 22 on a lateral side of the boot 20. The boot connection point 22 is not limited to the lateral side of the boot 20; rather, it may be located anywhere on the boot 20.

As described above, the knee brace 10 and boot 20 are attachable and detachable via the first and second coupling elements 34, 36 of the tether member 38. The first and second coupling elements 34, 36 are attachable and detachable via cooperatively engageable first and second linking portions 30, 32. According to an embodiment, the first and second linking portions 30, 32 are cooperatively engageable male and female linking structures, where the male linking structure is included on the first coupling element 34, and the female linking structure is included on the second coupling element 36. However, alternative embodiments may include the female linking structure on the first coupling element 34 and the male linking structure on the second coupling element 36. There may also be alternative embodiments of the first and second linking portions 34, 36, which may include fasteners known by those skilled in the art, including hook and loop fasteners, and buckle and strap fasteners. In addition, there may be other embodiments of the invention in which one of the first or second linking portions 30, 32 is a slot and the other linking portion may pass through the slot and engages with itself. For example, the second linking portion 32 may be a slot, and the first linking portion 30 may have both hook and loop fasteners located on it. In such an embodiment the hook fasteners of the first linking portion 30 pass through the slot of the second linking portion 32, and engage with loop fasteners located on the first linking portion 30.

The tether member 38 connects the knee brace 10 and the boot 20. According to various embodiment of the present invention, the tether member may take on many different forms. As was mentioned above, the tether member may include male and female linking structures. FIG. 2 is a side view of an embodiment of the present invention having a rigid tether member 38. The tether body portion 28 shown in FIG. 2 is rigid compared to the tether body portion 28 shown in FIG. 1, which may be flexible. For a discussion of flexible tether members, see U.S. patent application Ser. No. 11/396,886 which is incorporated by reference.

A rigid tether member 38 fully integrates the knee brace 10 with the boot 20. As such, the tether member 38 restricts the rotation of the knee brace 10 relative to the boot 20. Therefore, when a rotational force is applied to the boot 20, the knee brace 10 will rotate with the boot 20, thereby safely transmitting the rotational force to the user's thigh and protecting the user's knee ligaments.

In another embodiment of the present invention, the tether member may be a push-pin, as is shown in FIGS. 3 and 4. As used herein, a push-pin includes a body portion and a spring-loaded locking mechanism 40. The body portion of the push pin extends through the knee brace and boot. The knee brace 10 and boot 20 shown in FIGS. 3 and 4 have holes located at the boot and brace connection points 22, 18. The push pin extends transversely through the center of the holes located at the boot and brace connection points 22, 18. When the push pin is fully extended through the holes, the spring-loaded locking mechanism 40 holds the push pin firmly in place. When the push pin is in place, the boot 20 and knee brace 10 may be freely flexed in the forward and rearward positions, while at the same time preventing the boot 20 and knee brace 10 from rotating relative to one another.

Figure 5:
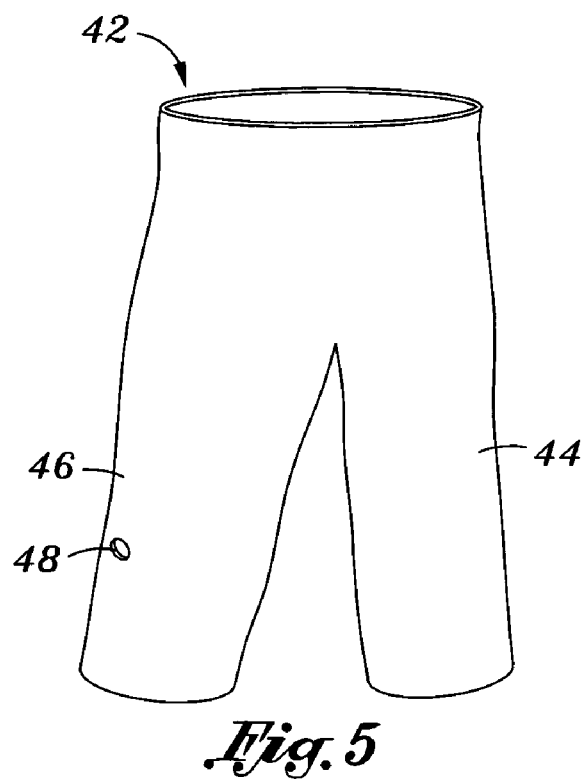
FIG. 5 is a perspective view of a pair of protective pants, the pants comprised of a left pant leg, a right pant leg, and a connection aperture located on at least one of the left and right pant legs.
Figure 6:
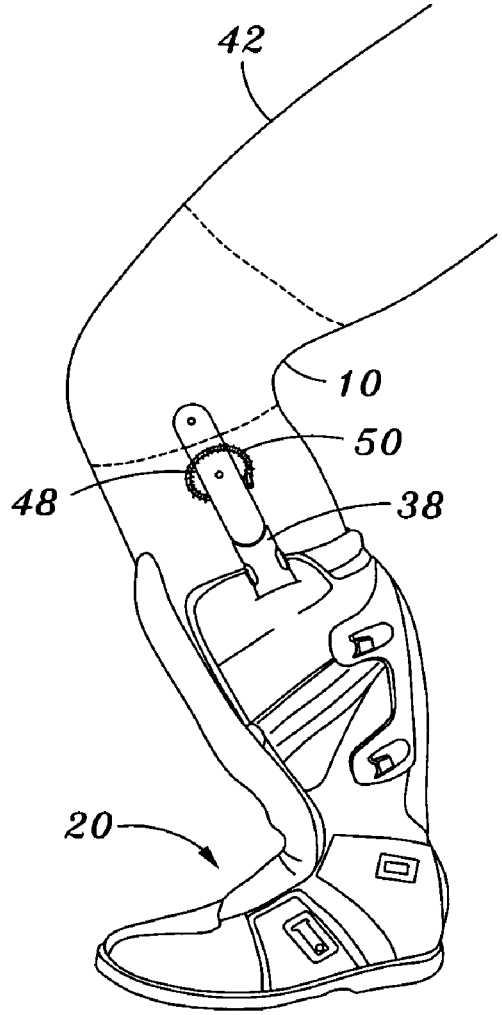
FIG. 6 is a perspective view of a pant leg from a pair of protective pants, the pant leg having a connection aperture located adjacent to a user's knee, the connection aperture having a closing mechanism.

It is understood that a knee brace 10 may be used in a number of different applications. In many of those applications, the user may choose to wear clothing over the knee brace 10. FIGS. 5 and 6 illustrate clothing designed to allow a tether member 38 to pass freely through the clothing. FIG. 5 is an illustration of a pair of protective pants 42. The protective pants 42 are intended to be worn over a knee brace 10. The protective pants 42 include a left pant leg 44 and a right pant leg 46 coupled to the left pant leg 44. The pants 42 also include a connection aperture 48 located on at least one of the left and right pant legs 44, 46. The connection aperture 48 is a slot in the pants 42 that allows the tether member 38 to pass from the knee brace 10 to the boot 20. The connection aperture 48 may simply be a slot in the pants 42. In this case, the aperture 48 would always be open, whether the user was wearing a knee brace or not. Alternatively, the connection aperture 48 may be fitted with a closing mechanism 50, allowing the user to close the aperture 48 when it is not needed. FIG. 6 shows a connection aperture 48 having a closing mechanism 50. The closing mechanism 50 shown in FIG. 6 is a zipper, however, buttons, snaps, and other known means of closing the aperture 48 may be used.

Figure 7:
FIG. 7 is a top view of a pair of reinforcement strips, the reinforcement strips comprised of a fabric material having a bonding agent disposed thereon.

The normal wear and tear on a connection aperture 48 may force the aperture 48 to tear or become worn. As such, according to another aspect of this invention, there is provided a reinforcement strip for repairing the connection aperture 48 as shown in FIG. 7. The reinforcement strip 52 includes a fabric material having a bonding agent disposed thereon. According to an aspect of the present invention, the bonding agent may be glue or other fastening agents known by those skilled in the art.

It is understood that athletes, motocross riders in particular, have been wearing knee braces 10 and boots 20 for some time. Therefore, the present invention is capable of being retrofitted onto a user's existing knee brace 10 and boot 20 at the brace and boot connection points 18, 22, respectively. For a discussion of retrofitting, see U.S. patent application Ser. No. 11/396,886 which is incorporated by reference.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A device for protecting ligaments in a knee joint of a user, the device comprising:
   a knee brace positionable about the knee joint of the user, the knee brace including:
      an upper frame member;
      a lower frame member having a brace connection point; and
      a joint member pivotally connected to the upper and lower frame members;
   a boot wearable on the foot of the user, the boot having a boot connection point; and
   a tether member having a first coupling element coupled to the knee brace at the brace connection point and a second coupling element coupled to the boot at the boot connection point, the first coupling element including a first fastening portion and a first linking portion, the first fastening portion coupling the first coupling element with the knee brace at the brace connection point, the second coupling element including a second fastening portion and a second linking portion, the second fastening portion coupling the second coupling element with the boot at the boot connection point, the first and second linking portions being cooperatively engageable, the boot and knee brace being attachable and detachable via the first and second coupling elements, the boot connection point being moveable relative to the brace connection point when the first and second coupling elements are attached.

2. The device of claim 1, wherein the first coupling element includes a tether body portion connected to the knee brace and a first linking portion translatably connected to the tether body portion, the first linking portion being engageable with the second coupling element.

3. The device of claim 2, wherein the first linking portion is rotatably connected to the tether body portion.

4. The device of claim 2, wherein the tether body portion is pivotally connected to the knee brace.

5. The device of claim 1, wherein the first coupling element includes a tether body portion connected to the knee brace and a first linking portion rotatably connected to the tether body portion, the first linking portion being engageable with the second coupling element.

6. The device of claim 5, wherein the tether body portion is pivotally connected to the knee brace.

7. The device of claim 1, wherein the first and second linking portions are male and female linking structures.

8. The device of claim 1, wherein the boot is a motorcycle boot.

9. A device for use with a boot having a boot connection point, the device being configured to protect ligaments in a knee joint of a user, the device comprising:
- a knee brace positionable about the knee joint of the user, the knee brace including:
  - an upper frame member;
  - a lower frame member having a brace connection point; and
  - a joint member pivotally connected to the upper and lower frame members; and
- a tether member having a first coupling element coupled to the knee brace at the brace connection point and a second coupling element connectable to the boot at the boot connection point, the first coupling element including a first fastening portion and a first linking portion, the first fastening portion coupling the first coupling element with the knee brace at the brace connection point, the second coupling element including a second fastening portion and a second linking portion, the second fastening portion coupling the second coupling element with the boot at the boot connection point, the first and second linking portions being cooperatively engageable, the boot and knee brace being attachable and detachable via the first and second coupling elements, the boot connection point being moveable relative to the brace connection point when the first and second coupling elements are attached.

10. The device of claim 9, wherein the first coupling element includes a tether body portion connected to the knee brace and a first linking portion translatably connected to the tether body portion, the first linking portion being engageable with the second coupling element.

11. The device of claim 10, wherein the first linking portion is rotatably connected to the tether body portion.

12. The device of claim 10, wherein the tether body portion is pivotally connected to the knee brace.

13. The device of claim 9, wherein the first and second linking portions are male and female linking structures.

14. The device of claim 9, wherein the first coupling element includes a tether body portion connected to the knee brace and a first linking portion rotatably connected to the tether body portion, the first linking portion being engageable with the second coupling element.

15. The device of claim 14, wherein the tether body portion is pivotally connected to the knee brace.

16. A device for protecting ligaments in a knee joint of a user, the device comprising:
- a knee brace positionable about the knee joint of the user, the knee brace including:
  - an upper frame member;
  - a lower frame member having a brace connection point; and
  - a joint member pivotally connected to the upper and lower frame members;
- a boot wearable on the foot of the user, the boot having a boot connection point; and
- a tether member having:
  - a first coupling element coupled to the knee brace at the brace connection point, the first coupling element includes a first fastening portion and a first linking portion, the first fastening portion coupling the first coupling element with the knee brace at the brace connection point; and
  - a second coupling element coupled to the boot at the boot connection point, the second coupling element includes a second fastening portion and a second linking portion, the second fastening portion coupling the second coupling element with the boot at the boot connection point, the first and second linking portions being cooperatively engageable, the boot and knee brace being attachable and detachable via the first and second coupling elements;
  - wherein the first linking portion is a male linking structure, and the second linking portion is a female linking structure.

* * * * *